(12) United States Patent
Nagaoka et al.

(10) Patent No.: US 8,815,518 B2
(45) Date of Patent: Aug. 26, 2014

(54) KIT FOR DETECTION/QUANTIFICATION OF ANALYTE, AND METHOD FOR DETECTION/QUANTIFICATION OF ANALYTE

(75) Inventors: Hirokazu Nagaoka, Ichihara (JP); Noriyuki Ohnishi, Ichihara (JP); Kageaki Matsui, Ichihara (JP); Satoru Sugita, Matsudo (JP)

(73) Assignee: JNC Corporation, Tokyo (JP)

( * ) Notice: Subject to any disclaimer, the term of this patent is extended or adjusted under 35 U.S.C. 154(b) by 1036 days.

(21) Appl. No.: 12/306,178

(22) PCT Filed: Jun. 28, 2007

(86) PCT No.: PCT/JP2007/063044
§ 371 (c)(1),
(2), (4) Date: Aug. 25, 2009

(87) PCT Pub. No.: WO2008/001868
PCT Pub. Date: Jan. 3, 2008

(65) Prior Publication Data
US 2010/0062433 A1     Mar. 11, 2010

(30) Foreign Application Priority Data
Jun. 30, 2006  (JP) ................................ 2006-182265

(51) Int. Cl.
*G01N 33/53* (2006.01)
*C12Q 1/00* (2006.01)
*G01N 33/00* (2006.01)
*B01L 3/00* (2006.01)
*G01N 31/22* (2006.01)
*G01N 33/544* (2006.01)
*G01N 33/543* (2006.01)

(52) U.S. Cl.
CPC .... *G01N 33/54313* (2013.01); *G01N 33/54333* (2013.01)

USPC ............... 435/7.1; 435/4; 435/7.93; 422/430; 436/528

(58) Field of Classification Search
USPC ................ 435/4, 7.1, 7.93; 422/430; 526/306
See application file for complete search history.

(56) References Cited

U.S. PATENT DOCUMENTS 5,670,381 A    9/1997  Jou et al.
5,998,588 A *  12/1999  Hoffman et al. .............. 530/402
(Continued)

FOREIGN PATENT DOCUMENTS

JP    S53-24015    3/1978
JP    S58-11575    3/1983
(Continued)

OTHER PUBLICATIONS

Furukawa et al, Affinity selection of target cells from cell surface displayed libraries: a novel procedure using a thermo-responsive magnetic particles, 2003, Appl. Microbiol. Biotechnolog., 62, 478-483.*

(Continued)

*Primary Examiner* — Narayan Bhat
(74) *Attorney, Agent, or Firm* — Hoffmann & Baron, LLP

(57) ABSTRACT

Disclosed are a detection/quantification kit and a detection/quantification method for detecting/quantifying an analyte rapidly at a low cost and in a simple manner. Specifically, disclosed is a kit for detecting an analyte in a sample, comprising a first conjugate and a second conjugate, wherein the first conjugate comprises a first substance comprising a stimuli-responsive polymer and a first affinity substance having affinity for the analyte and bound to the first substance, and the second conjugate comprises a second substance carrying an electrical charge and a second affinity substance having affinity for the analyte and bound to the second substance. The first and second affinity substances can bind to different sites on the analyte simultaneously.

14 Claims, 10 Drawing Sheets

(56) References Cited

U.S. PATENT DOCUMENTS

| | | |
|---|---|---|
| 2003/0165962 A1* | 9/2003 | Furukawa et al. ............. 435/6 |
| 2006/0194887 A1* | 8/2006 | Kojima et al. ............. 516/113 |
| 2008/0200562 A1* | 8/2008 | Yin et al. ............. 514/772.3 |

FOREIGN PATENT DOCUMENTS

| | | |
|---|---|---|
| JP | 2005-82538 | 3/2005 |
| WO | WO 92/21980 A1 | 12/1992 |
| WO | WO 95/25282 A1 | 9/1995 |
| WO | WO 97/09068 A2 | 3/1997 |
| WO | WO 00/11473 A1 | 3/2000 |
| WO | 0109141 | 2/2001 |
| WO | WO 2004/072258 A2 | 8/2004 |
| WO | WO 2007/137418 A1 | 12/2007 |

OTHER PUBLICATIONS

Data sheet ZZ domain, downloaded from the internet [URL: http://www.ncbi.nlm.nih.gov/protein/2SPZ_A], printed on Apr. 9, 2011, p. 1.*

Nagaoka et al, Coupling Stimuli-Responsive Magnetic Nanoparticles with Antibody Antigen Detection in Immunoassays, 2011, Anal. Chem., 83, 9197-9200.*

Supplementary European search report and the European search opinion issued to European Application No. 07767836.5, mailed Jun. 29, 2009.

Hoffman A S et al: "Really smart bioconjugates of smart polymers and receptor proteins" Journal of Biomedical Materials Research Dec. 2000 John Wiley and Sons Inc. US, vol. 52, No. 4, Dec. 2000, pp. 577-586, XP002211216.

Torchilin V P: "Polymeric Contrast Agents for Medical Imaging" Current Pharmaceutical Biotechnology, Bentham Science Publishers, NL, vol. 1, No. 2, Sep. 1, 2000, pp. 183-215, XP001155600 ISSN: 1389-2010.

Auditore-Hargreaves K et al: "Phase-separation immunoassays." Clinical Chemistry Sep. 1987, vol. 33, No. 9, Sep. 1987, pp. 1509-1516, XP002532182 ISSN: 0009-9147.

Monji N et al: "Application of a Thermally-Reversible Polymer-Antibody Conjugate in a Novel Membrane-Based Immunoassay" Biochemical and Biophysical Research Communications, Academic Press Inc. Orlando, FL, US, vol. 172, No. 2, Oct. 30, 1990, pp. 652-660, XP002034313 ISSN: 0006-291X.

Office Action issued to European Patent Application No. 07767836.5, mailed Oct. 4, 2011.

U.S. Appl. No. 12/810,038.

* cited by examiner

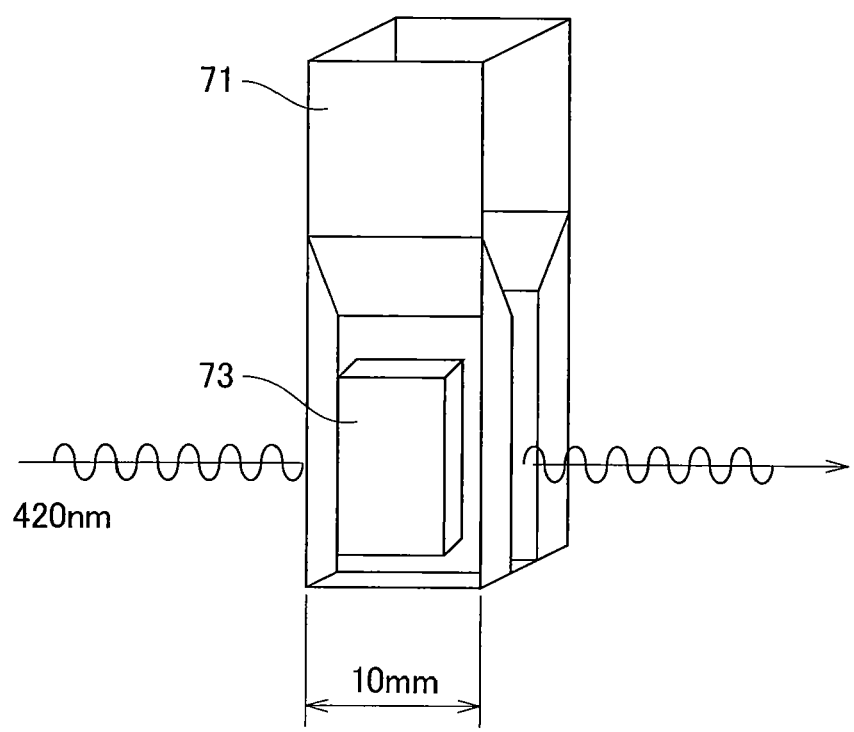

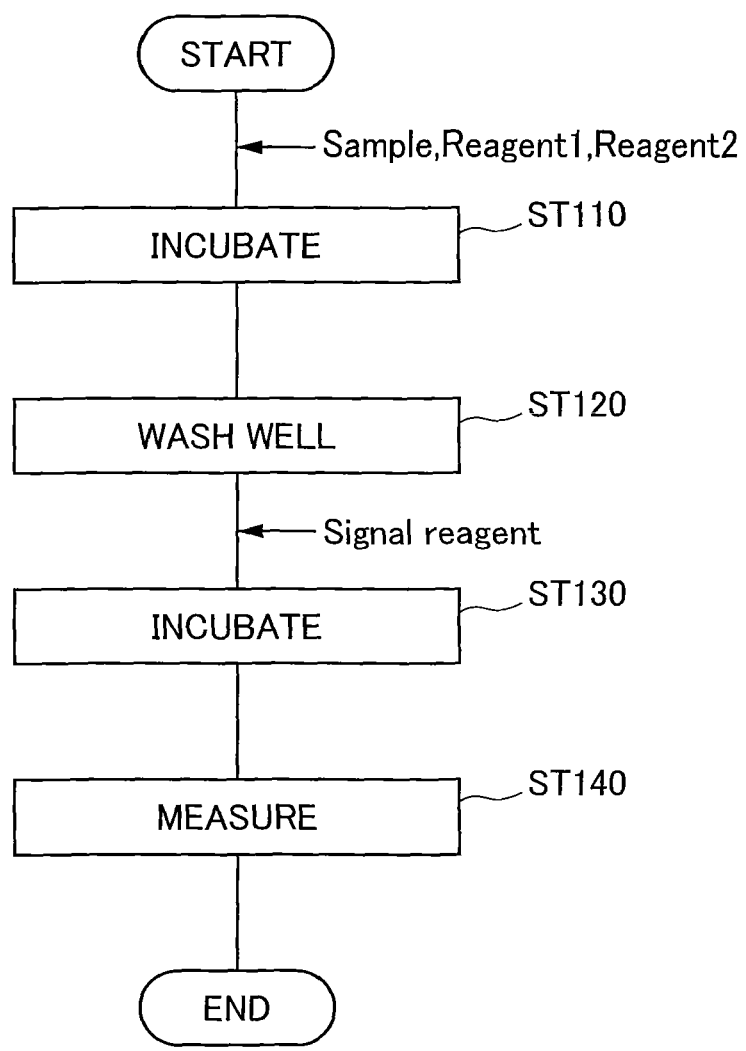

KIT FOR DETECTION/QUANTIFICATION OF ANALYTE, AND METHOD FOR DETECTION/QUANTIFICATION OF ANALYTE

CROSS-REFERENCE TO RELATED APPLICATIONS

This application is the National Stage of International Application No. PCT/JP2007/063044, filed Jun. 28, 2007, which claims the benefit of Japanese Application No. 2006-182265, filed Jun. 30, 2006, the contents of which is incorporated by reference herein.

TECHNICAL FIELD

The present invention relates to a method and kit for detecting and quantifying a target substance.

BACKGROUND ART

The latex aggregation method has long been used for detecting a target substance in a sample. In the latex aggregation method, in order to detect an antigen present in liquid such as a biological sample, the liquid and latex carrying the antibody or a fragment thereof that specifically binds to the target antigen are mixed, and the degree of latex aggregation is measured to detect or quantify the antigen (e.g., Patent Document 1).

According to the latex aggregation method, aggregation of latex is facilitated by an antigen, which is added as a sample and cross-links a plurality of latex-bound antibodies. This simple procedure allows for easy and rapid detection of an antigen. However, when the amount of the antigen is small, since it is difficult to generate cross-linking, a sufficient amount of latex cannot aggregate. Therefore, it was difficult to detect a small amount of antigen.

Thus, methods utilizing an enzyme-substrate reaction, such as ELISA and CLEIA, are widely adopted. In these methods, for example, a primary antibody that specifically to an antigen is bound to an antigen, and a secondary antibody having an enzyme is bound to this primary antibody. Then, an enzyme substrate is added and the reactivity of enzyme catalysis is measured to detect or quantify an antigen.

According to these methods, by using a luminescent reagent as a substrate for example, the high detectability of a luminous reaction after adding the substrate allows detection of a small amount of antigen.

Patent Document 1: Japanese Examined Application Publication No. 58-11575

DISCLOSURE OF THE INVENTION

Problems to be Solved by the Invention

However, the methods utilizing an enzyme-substrate reaction require special reagents and instruments such as a secondary antibody, luminescent reagent and photodetector, which make the operating cost high.

Moreover, as shown in FIG. 10, these methods consist of a plurality of steps that make the operation complex, such as incubation of the specimen and each reagent (ST110 and ST130), cleaning of the system (ST120), and detection of the luminous reaction (ST140). Each of these steps takes an extremely long time, and therefore these methods are not suitable for large-scale processing.

The present invention was developed in view of the above-mentioned situation. One object of the present invention is to provide a kit and a method for detecting and quantifying a target substance that allows for rapid, inexpensive and convenient detection and quantification of a target substance. Another object of the present invention is to provide a kit and a method for detecting and quantifying a target substance that allows for highly sensitive detection and determination.

Means for Solving the Problems

The inventors found that the aggregation of stimuli-responsive polymer is inhibited when an electrically charged compound is brought in close proximity, to accomplish the present invention. Specifically, the present invention provides the following.

According to a first aspect of the present invention, a kit for detecting a target substance, including a first bound substance in which a first substance containing a stimuli-responsive polymer binds to a first affinity substance having affinity to the target substance, a second bound substance in which a second electrically charged substance binds to a second affinity substance having affinity to the target substance, in which the first affinity substance and the second affinity substance can bind simultaneously to different sites of the target substance.

According to a second aspect of the present invention, in the kit according the first aspect of the present invention, the first substance contains a particulate magnetic material.

According to a third aspect of the present invention, in the kit according to the first or second aspect of the present invention, the second substance is a hydrophilic polymer compound.

According to a fourth aspect of the present invention, in the kit according to any one of the first to third aspects of the present invention, the second substance is a polyanion or a polycation.

According to a fifth aspect of the present invention, in the kit according to the fourth aspect of the present invention, the polyanion is a nucleic acid or a polyacrylic acid.

According to a sixth aspect of the present invention, in the kit according to the fourth aspect of the present invention, the polycation is a polyalkylamine or a polyethyleneimine.

According to a seventh aspect of the present invention, a method for detecting a target substance in a sample comprises steps of: mixing a first bound substance in which a first substance containing stimuli-responsive polymer binds to a first affinity substance having affinity to the target substance, a second bound substance in which a second electrically charged substance binds to a second affinity substance having affinity to the target substance, and the sample; putting the mixture under aggregation conditions of the stimuli-responsive polymer, and determining if the stimuli-responsive polymer is dispersed or not, wherein the first affinity substance and the second affinity substance can simultaneously bind to different sites of the target substance.

According an eighth aspect of the invention, in the method according to the seventh aspect of the present invention, the first substance contains a particulate magnetic material, and the method further includes a step of separating the aggregated magnetic material by applying a magnetic force.

According a ninth aspect of the present invention, a method for quantifying a target substance in a sample includes steps of: mixing a first bound substance in which a first substance containing stimuli-responsive polymer binds to a first affinity substance having affinity to the target substance, a second bound substance in which a second electrically charged substance binds to a second affinity substance having affinity to the target substance, and the sample; putting the mixture under aggregation conditions of the stimuli-responsive polymer, and measuring the turbidity of the mixture; and calculating the amount of a target substance in the sample based on a correlation equation between the amount of the target substance and the turbidity under the aggregation conditions.

According to a tenth aspect of the present invention, in the method according to the ninth aspect of the present invention, the first substance contains a particulate magnetic material, and the method further includes a step of separating the aggregated magnetic material by applying a magnetic force.

Effects of the Invention

According to the present invention, if a target substance is present, a first affinity substance and a second affinity substance hind to the target. Therefore, a stimuli-responsive polymer bound to the first affinity substance and a second substance bound to the second affinity substance are brought close to each other. Thus, an electrically charged moiety is arranged in the vicinities of a stimuli-responsive polymer. Therefore, an aggregation of a stimuli-responsive polymer responding to stimulus is inhibited. Therefore, by observing an occurrence of the inhibition of aggregation, the presence or absence of the target substance can be detected. In addition, by measuring the degree of the inhibition of aggregation, the target substance can be quantified.

All of the abovementioned procedures can be conducted without particularly using any special reagent or instrument, and therefore are inexpensive and convenient. Also, the abovementioned procedures only measure the degree of the inhibition of aggregation and are not systems utilizing a reaction catalyzed by an enzyme, and therefore can be conducted quickly. Furthermore, since the electrically charged moiety of the second substance greatly inhibits the aggregation of stimuli-responsive polymer, high-sensitivity detection and quantification of the target substance become possible.

BRIEF DESCRIPTION OF THE DRAWINGS

FIG. 3 is a diagram showing an aspect of an application of magnetic force in a method according to an Example of the present invention;

FIG. 10 is a flow chart of a method according to the prior embodiment.

Figure 1:
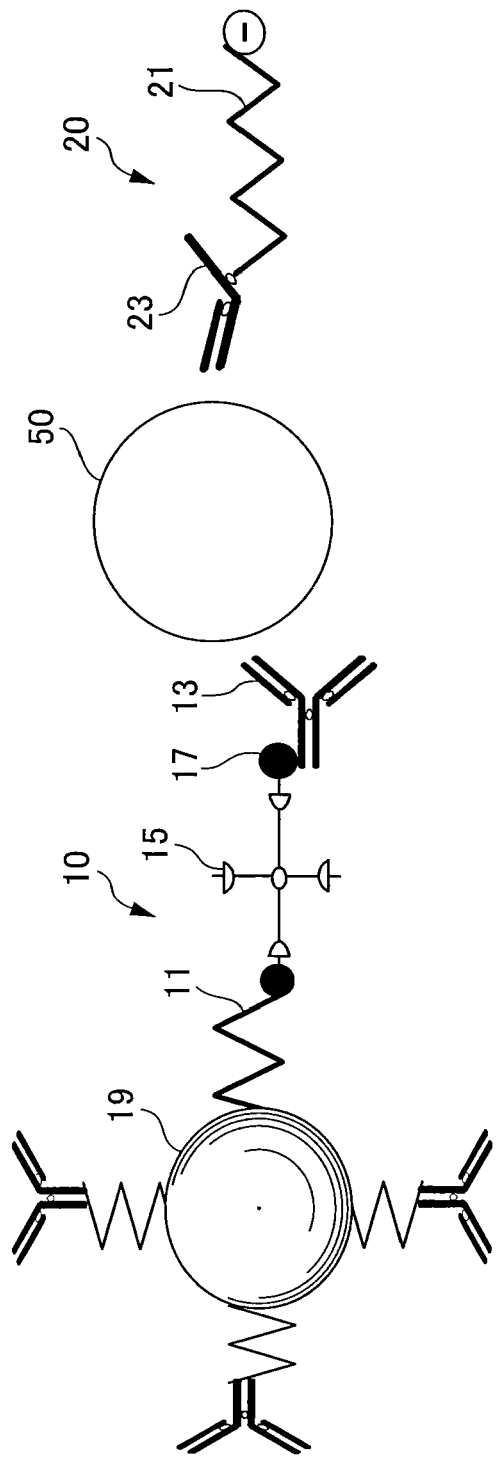
FIG. 1 is a schematic block diagram of the kit according to an embodiment of the present invention.

| EXPLANATION OF REFERENCE NUMERALS | |
|---|---|
| 10 | First bound substance |
| 11 | Stimuli-responsive polymer |
| 13 | First Antibody (First affinity substance) |
| 19 | Magnetic material |
| 20 | Second bound substance |
| 21 | Second substance |
| 23 | Second antibody (Second affinity substance) |
| 50 | Target substance |

PREFERRED MODE FOR CARRYING OUT THE INVENTION

Below, an example of the present invention is explained with reference to diagrams.

Kit

The kit of the present invention is a kit for detecting and/or quantifying a target substance including a first bound substance and a second bound substance. Next, each item is explained in detail.

First Bound Substance

The first bound substance is a substance in which a first substance containing a stimuli-responsive polymer binds to a first affinity substance having affinity to the target substance.

First Substance

The first substance used in the present invention contains a stimuli-responsive polymer which undergoes a conformation change in response to an external stimulus, thereby being a polymer that can adjust the aggregation and dispersion. The stimulus is not limited to a specific stimulus, but various physical or chemical signals such as temperature, light, acid, base, pH, electricity or the like can be used.

Particularly, in the present invention, a temperature-responsive polymer which is able to aggregate and disperse by temperature change is preferred as a stimuli-responsive polymer. Preferably, the stimuli-responsive polymer does not undergo a conformation change when it binds to a molecule having an electrical charge. The temperature-responsive polymer includes polymers which have a lower critical solution temperature (hereinafter referred as LCST), and polymers which have an upper critical solution temperature.

A polymer having a lower critical solution temperature used in the present invention includes: polymers having N-substituted (meth)acrylamide derivative such as N-n-propyl acrylamide, N-isopropyl acrylamide, N-ethylacrylamide, N,N-dimethyl acrylamide, N-acryloyl pyrrolidine, N-acryloyl piperidine, N-acryloyl morpholine, N-n-propyl methacrylamide, N-isopropyl methacrylamide, N-ethyl methacrylamide, N,N-dimethyl methacrylamide, N-methacryloyl pyrrolidine, N-methacryloyl piperidine and N-methacryloyl morpholine; polyoxyethylene alkyl amine derivatives such as hydroxypropyl cellulose, polyvinyl alcohol partial acetal, polyvinylmethyl ether, (polyoxyethylene-polyoxypropylene) block copolymer, and polyoxyethylenelauryl amine; polyoxyethylenesorbitan ester derivatives such as polyoxyethylenesorbitanlaurate; (polyoxyethylenealkylphenyl ether) (meth)acrylates such as (polyoxyethylene nonylphenylether) acrylate, (polyoxyethyleneoctylphenylether)methacrylate; and polyoxyethylene(meth)acrylic ester derivatives such as (polyoxyethylene alkyl ether)(meth)acrylate of (polyoxyethylenelauryl ether) acrylate, (polyoxyethyleneoleyl ether) methacrylate. Furthermore, these polymers and copolymers having at least 2 monomers of the above species can be used as well. In addition, a copolymer of N-isopropyl acrylamide and N-t-butyl acrylamide can also be used. When a polymer having (meth) acrylamide derivative is used, the polymer can be copolymerized with other copolymerizable monomers, as long as the monomers have a lower critical solution temperature. Particularly, in the present invention, polymers having at least one monomer selected from the group consisting of N-n-propyl acrylamide, N-isopropyl acrylamide, N-ethyl acrylamide, N,N-dimethylacrylamide, N-acryloyl pyrrolidine, N-acryloyl piperidine, N-acryloyl morpholine, N-n-propyl methacrylamide, N-isopropyl methacrylamide, N-ethyl methacrylamide, N,N-dimethyl methacrylamide, N-methacryloyl pyrrolidine, N-methacryloyl piperidine, and N-methacryloyl morpholine, or a copolymer of N-isopropyl acrylamide and N-t-butyl acrylamide are preferably used.

Polymers having an upper critical solution temperature used in the present invention include polymers having at least one monomer selected from the group consisting of acryloyl glycineamide, acryloyl nipecotamide, acryloyl asparagineamide, and acryloyl glutamineamide, and the like. In addition, copolymers including at least 2 monomers of these can be used as well. The abovementioned polymers can be copolymerized with other copolymerizable monomers such as acrylamide, acetyl acrylamide, biotinol acrylate, N-biotinyl-N'-methacryloyl trimethylene amide, acroyl sarcosineamide, methacryl sarcosineamide, acroyl methyluracil, etc. as long as having an upper critical solution temperature.

Particulate Magnetic Material

The particulate magnetic material used in the present invention can be constituted of a multivalent alcohol and magnetite. Any multivalent alcohol can be used without limitation, provided that it has at least two hydroxyl groups in constitutional units and can bind to an iron ion, for example, dextran, polyvinyl alcohol, mannitol, sorbitol, and cyclodextrin. For example, Japanese Unexamined Patent Application No. 2005-82538 discloses a method for manufacturing particulate magnetic material using dextran. Alternatively, a compound such as glycidyl methacrylate polymer, which has an epoxy group and forms multivalent alcohol structure after ring opening can be used as well. The particulate magnetic material (magnetic particles) prepared by multivalent alcohol preferably have a mean particle size of 0.9 nm to 1000 nm in order to ensure superior dispersion. Particularly, in order for the particles to increase ability to detect target substance recognition, the particles preferably have a mean particle size of at least 2.9 nm and less than 200 nm.

Second Bound Substance

The second bound substance is a substance in which an electrically charged second substance binds to a second affinity substance having affinity to the target substance.

Second Substance

The electrically charged second substance is a hydrophilic polymer compound, preferably a polyanion or a polycation. The polyanion indicates a substance which has a plurality of anion groups, and the polycation indicates a substance which has a plurality of cation groups. Examples of the polyanion include nucleic acids such as DNA and RNA. These nucleic acids have the property of a polyanion because they have a plurality of phosphodiester groups along the backbone of the nucleic acids. In addition, the polyanion includes a polypeptide (polypeptide consisting of amino acids such as glutamic acid and asparagine acid) containing many carboxylic acid functional groups, polyacrylic acid, polymethacrylic acid, polymers including acrylic acid or methacrylic acid as a polymerization component, and polysaccharide such as carboxymethylcellulose, hyaluronic acid and heparin. On the other hand, examples of the polycation include polylysine, polyarginine, polyornithine, polyalkylamine, polyethyleneimine, and polypropyl ethyleneimine, and the like. The number of functional groups of the polyanion (carboxyl group) or the polycation (amino group) is preferably at least 25.

First and Second Affinity Substances

The first affinity substance of the first bound substance and second affinity substance of the second bound substance are substances which can bind simultaneously to different sites of the target substance. For example, the first affinity substance and the second affinity substance may be a monoclonal antibody recognizing the different antigenic determinants of the target substance.

The antibody used in the present invention can be any type of immunoglobulin molecule, for example immunoglobulin molecule fragment which has an antigen binding site such as Fab and the antibody could be monoclonal or polyclonal, however preferably two different monoclonal antibody recognizing two different antigenic sites of the target substance.

Preparation Method

A method for preparing the abovementioned kit is hereafter explained.

Preparation of First Bound Substance

The first bound substance is prepared by binding the first substance and the first affinity substance. The binding method is not limited to a particular method; however, for example, substances having affinity to each other (e.g., avidin and biotin, glutathione and glutathione S-transferase) are bound to the first substance (for example, a stimuli-responsive polymer moiety) and to the first affinity substance (for example, the first antibody), and the first substance and the first affinity substance are bound to each other via these substances.

For example, as described in the booklet of WO 01/09141, biotin can be bound to the stimuli-responsive polymer by binding biotin or other affinity substances to a polymerizing functional group such as a methacryl group or acryl group to produce an addition polymerizable monomer, which further copolymerizes with other monomers. In addition, avidin or the other affinity substances can be bound to the first affinity substance by a common method. Then, by mixing a biotin-bound stimuli-responsive polymer and an avidin-bound first affinity substance, the first affinity substance and the stimuli-responsive polymer are bound to each other via binding between avidin and biotin.

As an alternative, during polymerization, a monomer having carboxylic acid or functional groups such as an amino group or epoxy group can be copolymerized with another monomer, and an antibody affinity compound (e.g., melon gel, protein A, protein G, etc.) can be bound to the polymer according to a well-known method. The antibody affinity substance thus obtained can be bound to the first antibody, to obtain a first bound substance in which the stimuli-responsive polymer binds to the first antibody of the target antigen.

Alternatively, during polymerization, a monomer having carboxylic acid or functional groups such as an amino group or epoxy group can be copolymerized with another monomer, and by a commonly known method, the first antibody related to the target antigen can be bound directly to these functional groups.

Alternatively, the first affinity substance and the stimuli-responsive polymer can be bound to the particulate magnetic material.

The first bound substance can be purified by putting the first substance containing the stimuli-responsive polymer under a condition where the stimuli-responsive polymer aggregates, followed by separating the aggregated polymer by centrifugation. The first bound substance can also be purified by binding the particulate magnetic material, and then the first affinity substance to the stimuli-responsive polymer, followed by collecting the magnetic material by applying a magnetic force.

The particulate magnetic material and the stimuli-responsive polymer can be bound by a method well-known in the art, such as a method binding through a reactive functional group, or a method for introducing unsaturated bond to the active hydrogen on the multivalent alcohol or multivalent alcohol itself in the magnetic substances to graft polymerize. See, ADV. Polym Sci., Vol. 4, p. 111, 1965; J. Polymer Sci., Part-A, 3, p 1031, 1965.

Next, a method for binding the electrically charged second substance and the second antibody of the target antigen to produce a second bound substance is described.

Preparation of Second Bound Substance

The second bound substance is prepared by binding directly or indirectly the second substance and the second affinity substance. The binding method is not limited to a particular method; however, for example, substances having affinity to each other (e.g., avidin and biotin, glutathione and glutathione S-transferase) are bound to both of the second substance and the second affinity substance (for example, the second antibody), and the second substance and the second affinity substance are indirectly bound to each other via the affinity substances.

When the second substance and the second affinity substance are directly bound, they can be bound via a functional group, for example, when using a functional group, maleimide-thiol coupling as in the method of Ghosh et al., (Ghosh et al.: Bioconjugate Chem., 1, 71-76, 1990) can be used. Specifically, the following two methods can be adopted.

According to a first method, a mercapto group (sulfhydryl group) is introduced into the 5' end of the nucleic acid, and a maleimide group is introduced to the antibody by reacting 6-maleimide hexanoic acid succinimide ester (e.g., EMCS (trade name) manufactured by DOJINDO LABORATORIES) with the antibody. Next, the abovementioned two substances are bound to each other via the mercapto group and the maleimide group.

According to a second method, a mercapto group is introduced to the 5' end of the nucleic acid, in a similar way to the first method. Then, the mercapto group is introduced to the antibody while N,N-1,2-phenylene di-maleimide, a homo bi-functional reagent, reacts with this mercapto group to introduce a maleimide group to the 5' end of the nucleic acid. Next, the abovementioned two substances are bound to each other via the mercapto group and the maleimide group.

Other methods known in the art to introduce nucleic acid to a protein include methods, for example, described in Nucleic Acids Research Vol. 15, p. 5275 (1987) and Nucleic Acid Research Vol. 16, p. 3671 (1988). These techniques can be applied for binding nucleic acid and antibody.

According to Nucleic Acids Research Vol. 16, p. 3671 (1988), oligonucleotide reacts with cystamine, carbodiimide, and 1-methylimidazole to introduce a mercapto group to the hydroxyl group at the 5' end of oligonucleotide. After purifying the oligonucleotide, to which the mercapto group is introduced, the oligonucleotide is reduced by using dithiothreitol. Subsequently, by adding 2,2'-dipyridyl disulfide, a pyridyl group is introduced to the 5' end of the oligonucleotide via disulfide bond. On the other hand, regarding the protein, a mercapto group is introduced by reacting iminothiolane. The oligonucleotide to which the pyridyl group is introduced and the protein to which mercapto group is introduced are mixed to react the pyridyl group and mercapto group specifically in order to bind the protein and the oligonucleotide.

According to Nucleic Acids Research Vol. 15, p. 5275 (1987), an amino group is introduced to the 3' end of the oligonucleotide, and reacted with the dithio-bis-propionic acid-N-hydroxysuccinimide ester (abbreviated name: dithio-bis-propionyl-NHS), which is a homo bi-functional reagent. After the reaction, dithiothreitol is added to reduce the disulfide bond in the dithio-bis-propionyl-NHS molecule, then a mercapto group is introduced to the 3' end of oligonucleotide. For treatment of the protein, a hetero bi-functional cross linking agent, as described in Japanese Unexamined Patent Application No. 5-48100, is used. First, the protein reacts with the hetero bi-functional cross-linking agent having a first reactive group (succinimide group) that can react with a functional group (e.g., amino group) in the protein and a second reactive group (e.g. maleimide group) that can react with a mercapto group. Then, the second reactive group is introduced to the protein to obtain a protein reagent activated in advance. The resulting protein reagent is bound covalently to the mercapto group of the thiolated polynucleotide.

When using a polyanion and polycation other than the nucleic acid, by introducing a mercapto group to the ends or the other parts thereof, a second bound substance can be prepared in a similar way to the above.

The resulting kit can be used to detect or quantify the target substance, for example, in the following ways.

Detection Method

The detection method according to the present invention includes steps of: mixing a first bound substance, a second bound substance, and the sample; putting the mixture under aggregation conditions of the stimuli-responsive polymer, and determining if the stimuli-responsive polymer is dispersed or not. Hereinafter, the steps are described in detail.

Mixing and Aggregation

To begin with, the first and the second bound substances are mixed, and then the sample is added, to obtain a mixture. Next, this mixture is put under the aggregation conditions of the stimuli-responsive polymer. Then, if the target substance is present, aggregation of the stimuli-responsive polymer is inhibited by the electrical charge of the second bound substance and the stimuli-responsive polymer disperses. If the target substance is not present, the stimuli-responsive polymer aggregates since no inhibition occurs.

This phenomenon is explained with reference to FIGS. 1, 2.

As shown in FIG. 1, a first bound substance 10 contains a stimuli-responsive polymer 11, and the stimuli-responsive polymer 11 is bound to a first antibody 13 for a target substance 50 via avidin 15 and biotin 17. Furthermore, the first bound substance 10 includes a particulate magnetic material 19, and the stimuli-responsive polymer 11 is bound to the surface of this magnetic material 19. On the other hand, a second bound substance 20 includes a negative charged second substance 21, and the second substance 21 is bound to a second antibody 23 for the target substance 50. Then, the first antibody 13 and second antibody 23 can be bound simultaneously to different sites of the target substance 50.

Figure 2A:
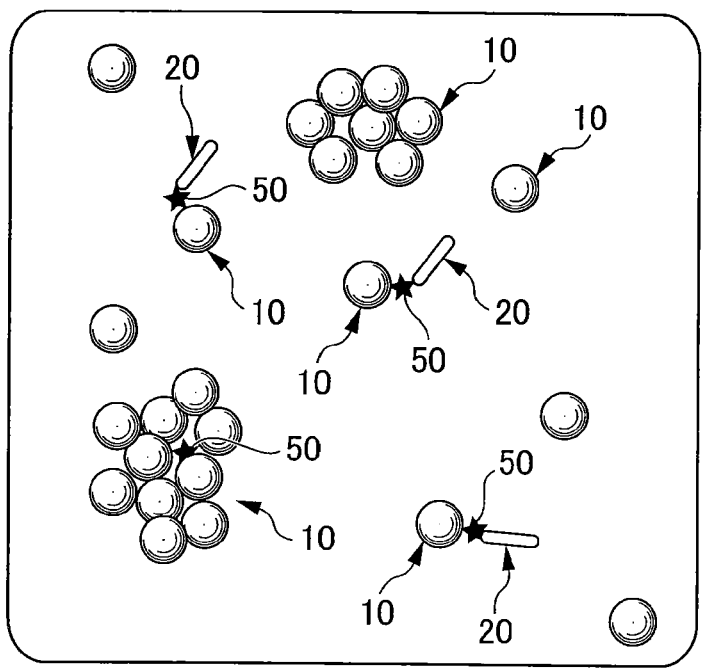
FIG. 2 is a schematic view showing a usage of the kit according to an embodiment of the present invention.
Figure 2B:
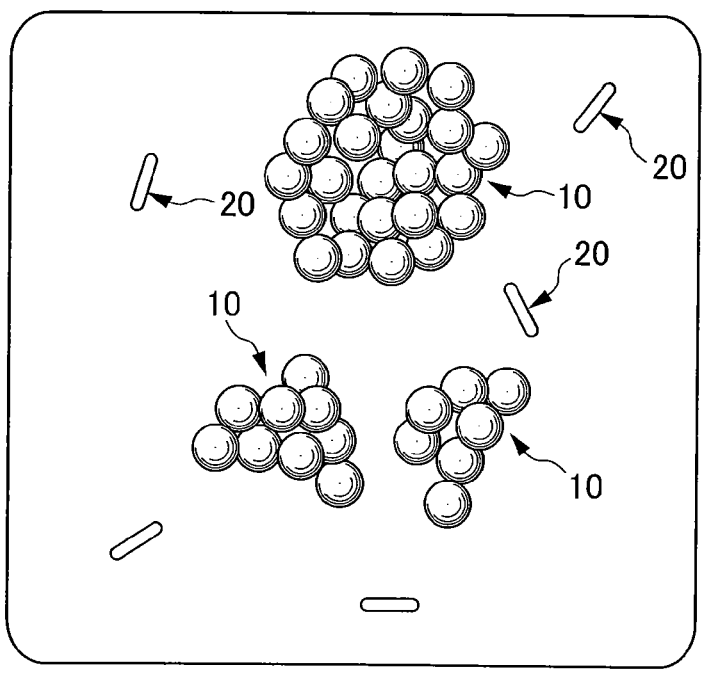

As shown FIG. 2, by putting a mixture of the first bound substance 10, the second substance 20, and the sample under predetermined conditions, in a case where the target substance 50 is present, aggregation of the stimuli-responsive polymer 11 is inhibited by the electrical charge of the second bound substance 20, and the stimuli-responsive polymer disperses (FIG. 2(A)). On the other hand, in a case where the target substance 50 is not present, the stimuli-responsive polymer 11 aggregates since no inhibition occurs (FIG. 2(B)).

To aggregate a stimuli-responsive polymer, for example, when a temperature-responsive polymer is used, the vessel containing the mixture can be moved to an incubator at the aggregation temperature of the temperature-responsive polymer. In addition, when a pH-responsive polymer is used, an acid solution or alkaline solution can be added to the vessel containing the mixture. Furthermore, when a light-responsive polymer is used, the vessel containing the mixture can be irradiated with light having a wavelength that can aggregate the polymer.

Note that the aggregation of the temperature-responsive polymer can take place simultaneously, before, or after binding to the first bound substance and the second bound substance; however, the latter should be preferred due to shorter processing time. However, if the aggregation conditions of the temperature-responsive polymer are greatly different from the conditions where the first bound substance and the second bound substance bind to a target substance, the former should be preferred.

For example, the lower critical solution temperature and the upper critical solution temperature are determined as follows. First, a sample is added to a cell of the absorptiometer, and heated at a rate of 1° C./min. During this period, the change in transmittance at 550 nm is recorded. The transmittance is 100% when a polymer is dissolved to be transparent, and 0% when completely aggregated. LCST is defined by determining the temperature where the transmittance is 50%.

Determination

The presence or absence of the dispersion can be confirmed, for example, visually or using turbidimetry. The turbidity can be calculated from the transmittance from a light scattering device. Low turbidity indicates that aggregation of the stimuli-responsive polymer is inhibited, and suggests the presence of the target substance. The wavelength of the light used in the present invention can be adjusted appropriately according to the particle size of the magnetic material, in order to obtain a desired detectability. The wavelength of the light is preferred to be in the range of visible light (e.g., 550 nm) so that conventional general-purpose devices can be used.

Visual observation or the turbidimetry may be carried out intermittently at regular intervals, or continuously over time. Also, the determination can be done based on the difference between turbidity measured at a certain point and turbidity measured at another point.

Quantitative Method

According to a method of the present invention, to begin with, a first bound substance, a second bound substance, and the sample are mixed, and the mixture is put under aggregation conditions of the stimuli-responsive polymer. Next, the turbidity of the mixture is measured to calculate the amount of a target substance in the sample based on a correlation equation relating the amount of the target substance and the turbidity under the aggregation conditions. An explanation is omitted for steps in the anterior half step in of this method, which is similar to the aforementioned detection method.

Correlation Equation

The correlation equation relating the amount of the target substance and the turbidity under the conditions same as the abovementioned aggregation conditions is made. The more measured data that is provided for the amount of the target substance and the turbidity constituting the correlation equation, the more reliable the correlation equation becomes. Thus, the data should be for at least 2 points of the target substance, and preferably for at least 3 points of the target substance.

Then, the correlation equation relating the amount of the target substance and the turbidity is not limited to be an equation indicating a direct correlation between the amount of the target substance and the turbidity, and can be a correlation equation relating parameters reflecting the amount of the target substance and the turbidity.

Calculation

The amount of the target substance in a sample can be calculated by assigning the measured turbidity of the mixture to the resulting correlation equation.

Separation

In a case where the first substance contains a particulate magnetic material, the detection method or quantitative method of the present invention preferably further includes a step of separating the aggregated magnetic material by applying a magnetic force. Thus, an aggregated magnetic material is separated from the foreign material including the magnetic material that is not aggregated. Therefore, the influence of the foreign material excluded, and then measured values such as the amount of separated magnetic material and the transmittance when the magnetic material is dispersed in a solvent reflect the presence of the target substance more consistently.

The application of a magnetic force can be performed by bringing a magnet close to the magnetic material. The magnetic force of the magnet depends on the magnitude of magnetic force of the magnetic material used. For example, a neodymium magnet by Magna Co., Ltd. can be used as the magnet.

The application of a magnetic force can be performed before or in parallel to the determination; however, simultaneous parallel processing is preferred so that time for processing can be reduced. It is supposed that the turbidity of mixture after separation should be relatively lower in the case of a mixture containing foreign material, since the aggregated magnetic material is separated from foreign material when a magnetic force is applied.

It should be noted that the term "turbidimetry" in a detection method or quantitative method includes not only measuring turbidity directly, but also measuring parameters reflecting turbidity. Such parameters include the difference of the turbidity measured at a plurality of points, the amount of separated aggregated substance, and the turbidity of the non-aggregated substance after the separation. One of the plurality of points is preferably the point near the point where the turbidity is a maximum after applying a magnetic force to the negative control in which a target substance is not present. Thus, the difference of the measured turbidity from the other points becomes larger, which allows for more accurate quantification of the target substance.

Target Substance

The target substance in a sample includes substances used for a clinical diagnosis such as, human immunoglobulin G, M, A and E, human albumin, human fibrinogen (fibrin and degradation product thereof), α-fetoprotein (AFP), C-reactive protein (CRP), myoglobin, carcinoembryonic antigen, hepatitis virus antigen, human chorionic gonadotropin (hCG), human placental lactogen (HPL), HIV antigen, allergen, bacterial toxin, bacterial antigen, enzyme, hormone (for example, human thyroid stimulating hormone (TSH) and insulin), and drugs that are contained in body fluid, urine, sputum or stool.

Exemplary Component and Usage of Kit

An exemplary component and usage of a kit for using in a method of the present invention are described below with an antigen as the target substance.

The reagent kit consists of the following reagents, for example.

The Antigen Detection Reagent Kit:

Reagent A: A temperature-responsive polymer to which a particulate magnetic material and a first antibody that binds specifically to the target antigen are bound Reagent B: An electrically charged compound in which a second antibody recognizes a site of the antigen different from the site recognized by the first antibody, and can bind to the target antigen simultaneously Reagent C: A standard sample of the substance to be measured (e.g., purified antigen)

Reagent D: A buffer for dilution (Buffer that can be used for dilution of the above reagent and the sample to be analyzed; for example, tris-chloride buffer or phosphate buffer)

In order to measure turbidity, a conventional well-known device to maintain the vessel at the aggregation temperature of the polymer, and a device to irradiate 200 to 900 nm transmitted light can be used.

The kit consisting of the above reagents can be used in a method as follows.

To begin with, 5 to 1000 microliters of reagent A and 5 to 1000 microliters of reagent B are mixed. To the solution containing the reagents A and B, (1) positive control containing a standard sample of the substance to be measured, (2) negative control with no additive, (3) a sample having 5 to 1000 microliters of a test solution are prepared to react at a temperature (for example about 0 to 30° C.) for a predetermined period. When a temperature-responsive polymer is used, each reaction mixture is added to a vessel kept at the aggregation temperature (e.g., 42° C.) of the polymer after the reaction. To the vessel, a transmitted light of 550 nm is irradiated to measure turbidity in order to determine presence or absence of the antigen or to quantify the antigen.

In an alternative method, reagents A and the above (1), (2) and (3) are reacted at a temperature at which the polymer disperses for a predetermined period. Then, reagent B is added and the resulting mixture is left for a predetermined period for reaction. The reaction solution is added to a vessel kept at an aggregation temperature. To the vessel, transmitted light of 550 nm is irradiated to measure the turbidity in order to determine the presence or absence of the antigen or to quantify the antigen.

EXAMPLES

Example 1

Preparation of Kit
Preparation of First Bound Substance

To begin with, an antibody (clone: M195, mouse IgG, produced by Leinco Technology, Inc.) which is the first affinity substance for the human thyroid stimulating hormone (TSH) which is a detection target, was biotinylated by a conventional well-known sulfo-NHS-Biotin method (by Asahi Techno Glass Corporation), and biotinylated anti-TSH beta antibody was prepared.

On the other hand, 250 microliters of Therma-Max LSA Streptavidin (by Magnabeat Corporation, 0.4 mass %), which is a streptavidin-bound particulate magnetic material, was placed into a 1.5 mL microtube. Then, the microtube was heated up to 42° C. to aggregate Therma-Max LSA Streptavidin. The aggregated substance was collected using a magnet, and the supernatant was removed. 250 microliters of another TBS buffer (20 mM Tris-HCl, 150 mM NaCl, pH 7.5) was added. The tube was cooled to disperse the aggregated substance. 50 microliters of the biotinylated anti-TSH beta antibody (0.75 mg/mL) dissolved in PBS buffer (0.01 M phosphoric acid buffer, 0.0027 M potassium chloride, 0.137 M sodium chloride, pH 7.4) was added to the dispersed fluid, and mixed end over end for 15 minutes at room temperature. The microtube was heated up to 42° C. to aggregate Therma-Max LSA Streptavidin, and the aggregated substance was collected using a magnet, and the supernatant was removed. Thus, excessive biotinylated anti-TSH beta antibody was separated (B/F separation). 250 microliters of TBS buffer was added, and the aggregated substance was dispersed by cooling. Next, an excessive amount of biotin was added to coat biotin binding sites of the streptavidin, and then excessive biotin was separated (B/F separation). Then, the first bound substance was prepared by dispersing the mixture in a PBS buffer (pH 7.4) solution including 0.5% (w/v) of BSA (manufactured by Sigma, Co.), 0.5% (w/v) of Tween (Registered Trademark) 20 and 10 mM EDTA.

Preparation of Second Substance

To begin with, 6 mg of 2-mercaptoethanol was added to 1 mL of an antibody (clone: M176, mouse IgG, produced by Leinco Technology, Inc., 1 mg/mL), which is the second affinity substance for the human thyroid stimulating hormone (TSH) that is a detection target, and reacted at 37° C. for 120 minutes. After the reaction, using Slide-A-Lyzer (trade name) dialysis cassette of 10K MWCO (Pierce), the mixture was dialyzed against 500 mL of PBS buffer to remove the excess 2-mercaptoethanol, and was concentrated to 0.5 mL using an ultrafilter with a 10K molecular weight cut-off limit (Amicon Ultra-4Ultracel 10k manufactured by Millipore Corporation) to obtain a reduced antibody of mouse anti-TSH alpha antibody. 0.5 mL of the reduced antibody and 100 microliters of maleimidated sodium polyacrylate (33 mg dissolved in 1 mL of PBS buffer) were reacted overnight at 4° C., then gel-filtrated using Superdex-200 10/300GL (manufactured by GE Healthcare) to obtain the labeled antibody. The labeled antibody (also called polyacrylic acid anti-TSH alpha antibody bound substance) was diluted with a solution containing 0.5% (w/v) of BSA (a product made in Sigma Company), 0.5% (w/v) of Tween 20 (Registered Trademark)/PBS (pH 7.4) and 10 mM EDTA to prepare the second bound substance.

The maleimidated sodium polyacrylate was prepared as follows.

To begin with, a 100 mL three-neck flask with a nitrogen gas introduction tube, a thermometer, and a stirrer were provided, 2 g of acrylic acid (manufactured by Wako Pure Chemical Industries, Ltd.), 0.021 g of 2-aminoethanethiol (manufactured by Wako Pure Chemical Industries, Ltd.) and 0.023 g of azobisisobutyronitrile (manufactured by Wako Pure Chemical Industries, Ltd.) were dissolved in 50 mL of N,N-dimethylformamide, and substituted with nitrogen for one hour. Then, the polymerization reaction was performed at 70° C. for seven hours. The resulting reaction mixture was concentrated under reduced pressure to 10 mL, then reprecipitated with diethyl ether until the viscous solution became powdery. A white precipitate was filtered, and then dried in a vacuum dryer overnight to obtain amino group-terminated polyacrylic acid (yield: 1.5 g). Subsequently, amino group-terminated polyacrylic acid was maleimidated. In a 50 mL recovery flask with a nitrogen gas introduction tube and a stirrer were provided, 0.5 g of amino group-terminated polyacrylic acid was dissolved in 10 mL of N,N-dimethylformamide. 3 mg of EMCS(N-(6-Maleimidocaproyloxy)succinimide) (manufactured by DOJINDO LABORATORIES) was added and reacted overnight. The resulting reaction mixture was vacuum concentrated to 1 mL, then reprecipitated with diethyl ether until the viscous-shaped solution became powdery. A white precipitate was filtered, and then dried in a vacuum dryer overnight to obtain maleimide group-terminated polyacrylic acid. The molecular weight was approximately 130,000 (manufactured by Tosoh Corporation, TSK-gel Super AW3000, 6 mm ID×150 mm, mobile phase 0.1 M sodium nitrate), and the yield was 0.4 g.

Preparation of Sample

Human thyroid stimulating hormone (TSH, manufactured by Aspen Bio Pharma, Inc., activity 8.51 U/mg, WHO80/558) was dissolved in PBS buffer (pH 7.4) at a concentration of 30 micrograms/mL. This solution was diluted with Vitros TSH calibrator 1 (TSH 0 μIU/ml, manufactured by Ortho-Clinical Diagnostic K.K.) to concentrations of 0.06 mIU/L, 0.0012 mIU/L and used as sample.

Quantification

As shown in FIG. 3, a neodymium permanent magnet 73 (manufactured by Seiko Sangyo Co., Ltd.) of 5 mm×9 mm×2 mm was attached outside the optical path of semi-microcell 71 for a spectrophotometer which is conventionally used. The cell 71 was installed in a visible-ultraviolet spectrophotometer UV-3101PC (manufactured by Shimadzu Corporation) provided with a cell temperature control unit, and held for more than 10 minutes at 37° C.

Figure 4:
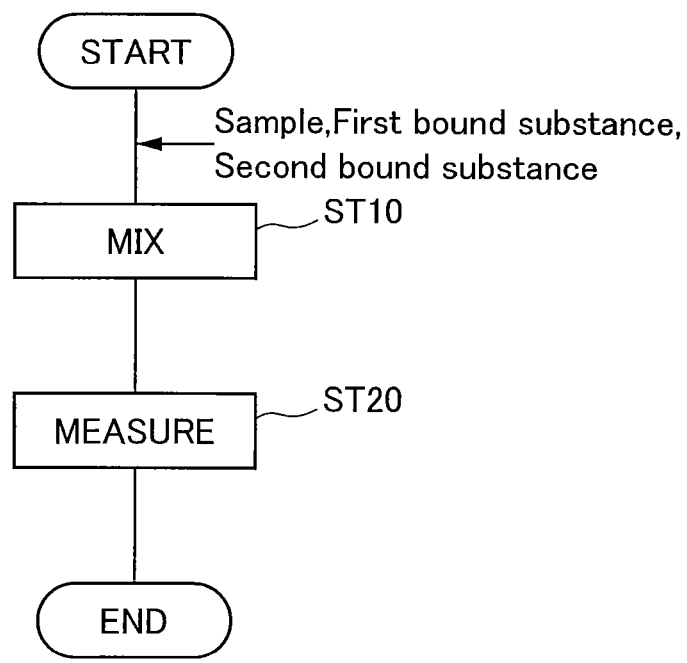
FIG. 4 is a flow chart of a method according to an Example of the present invention.

FIG. 4 is the flow chart of a method according to the Example. The quantitative method includes steps of mixing the first bound substance, the second bound substance and the sample (ST10), and determining the turbidity of the mixture (ST20).

Mixing 150 microliters of the first bound substance and 120 microliters of the second bound substance were poured into microtubes, and agitated with vortex mixer for one second. 750 microliters of each sample were added to the microtube, and further agitated with a vortex mixer for 60 seconds.

Derivation of Correlation Equation

The agitated solution was dispensed to the cell 71, and after zeroing the spectrophotometer according to the instruction manual thereof, was continually measured for 1200 seconds with light of which the wavelength was 420 nm with a 10 mm slit width. The results are shown in FIG. 5.

Figure 5:
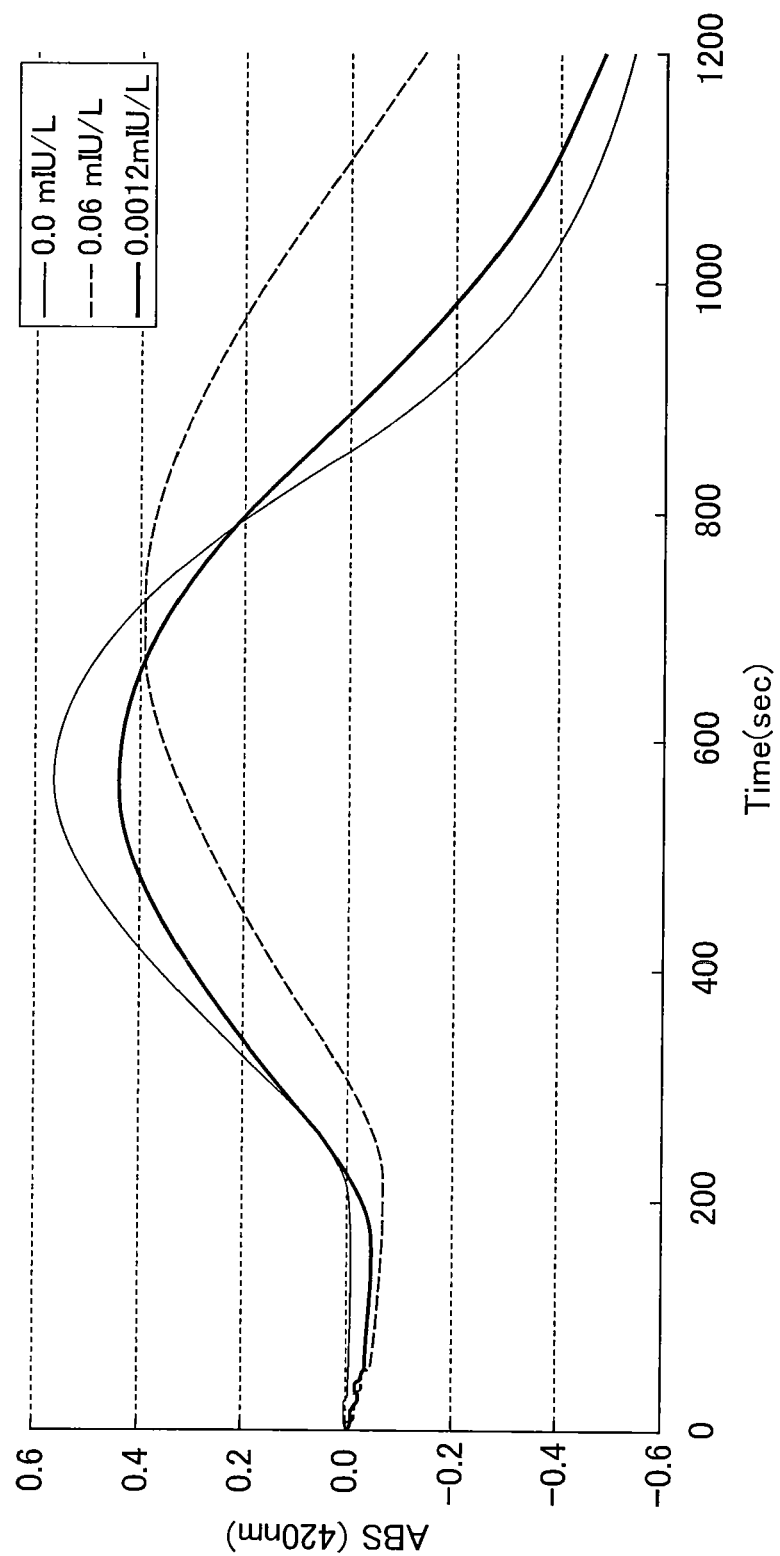
FIG. 5 is a graph showing a correlation between reaction time and turbidity in a method according to an Example of the present invention.

As shown in FIG. 5, until approximately 600 seconds, the more TSH present, the turbidity was the lower. This is because the stimuli-responsive polymers were arranged in the vicinity around TSH, and dispersed since aggregation thereof was inhibited by the electric charge of the second bound substance. However, the relation between the amount of TSH and the turbidity began to be reversed from approximately 600 seconds. The turbidity became lower than the initial value with time. This is because the aggregated magnetic material was separated by being attracted by the magnet.

Next, regarding each sample, the difference of the measured values between three points were observed: 0 seconds, 600 seconds, and 1000 seconds. These results are shown in FIGS. 6 to 8.

Figure 6:
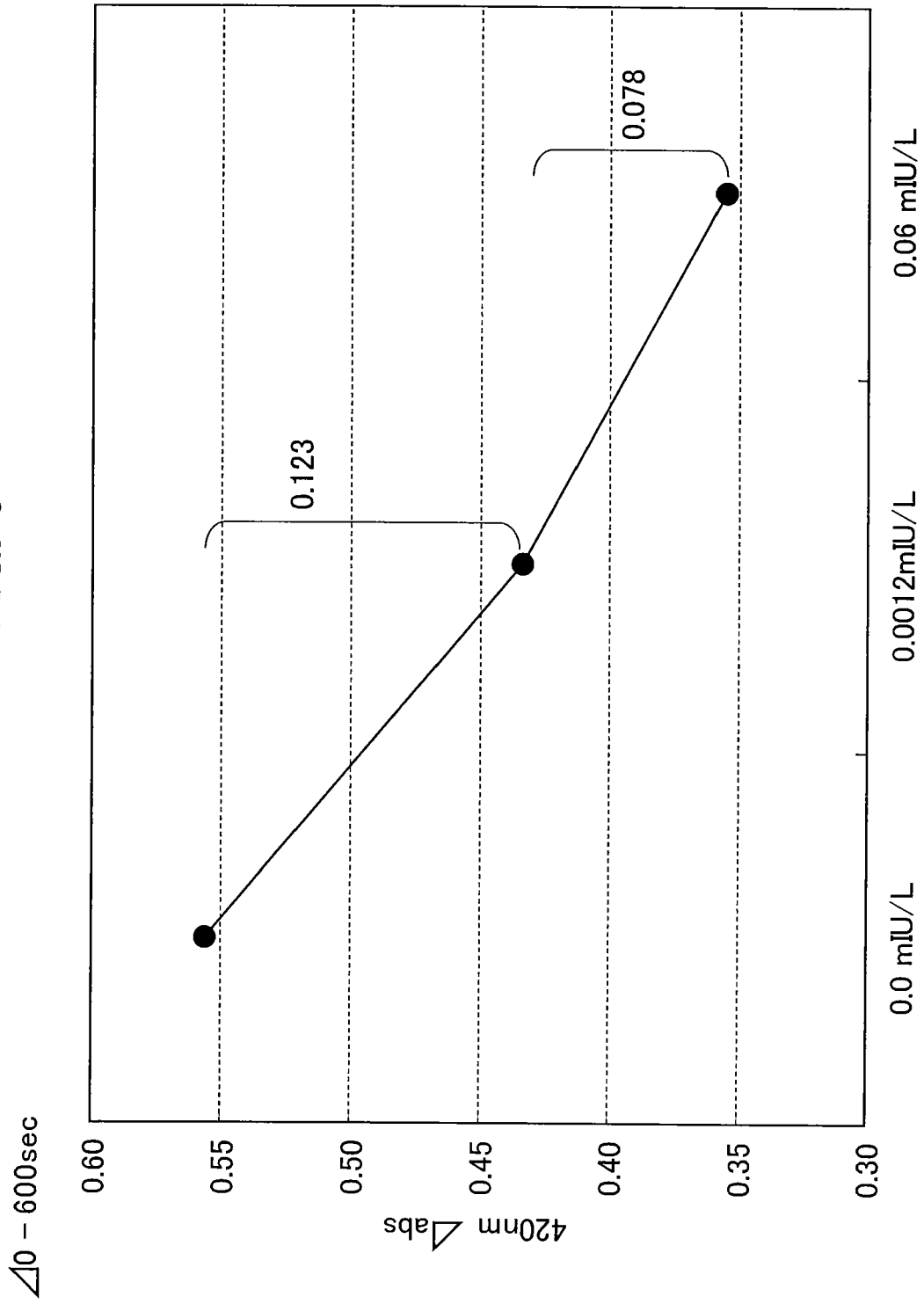
FIG. 6 is a graph showing a correlation between the amount of the target substance and turbidity in a method according to an Example of the present invention.
Figure 7:
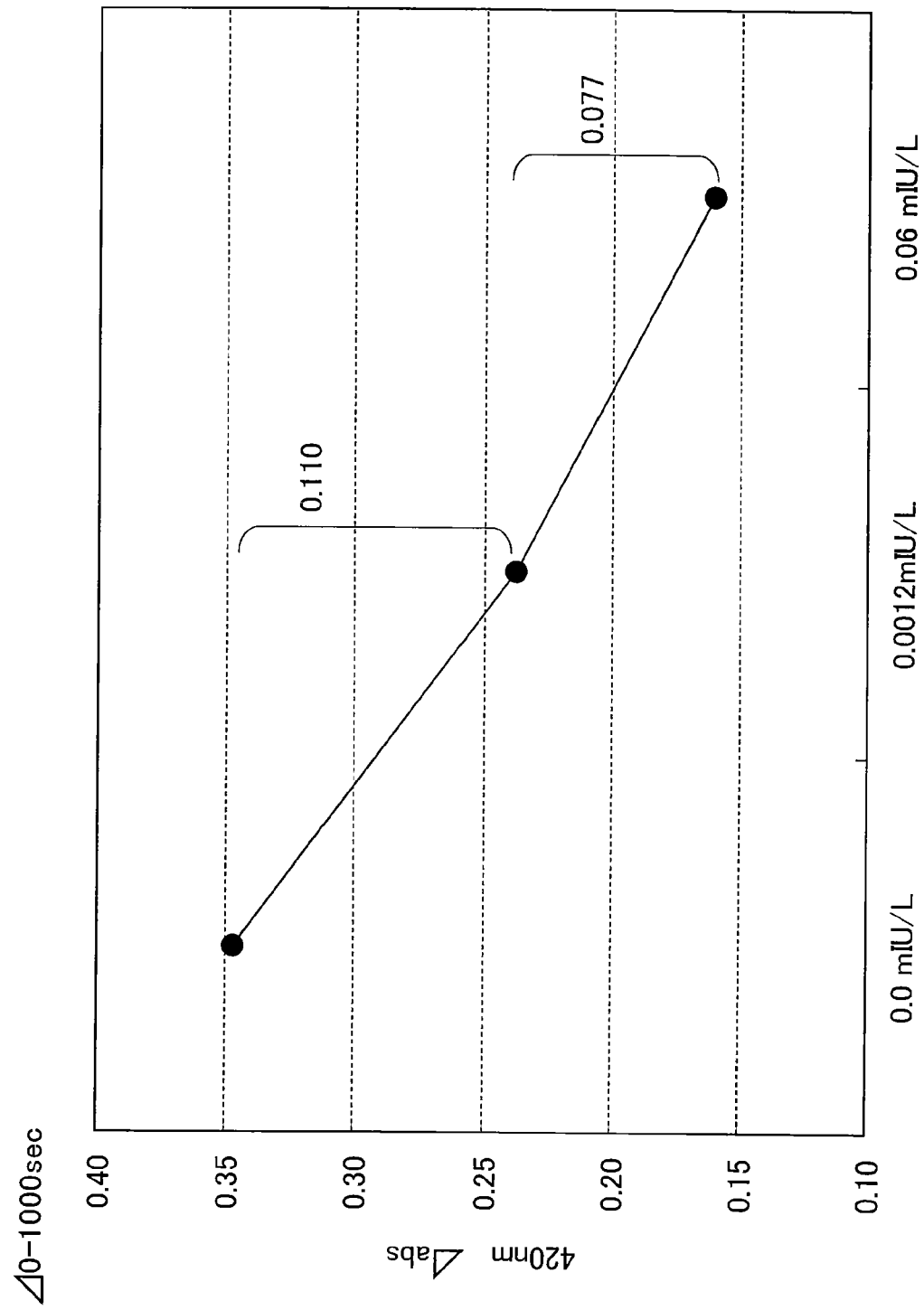
FIG. 7 is a graph showing a correlation between the amount of the target substance and turbidity in a method according to an Example of the present invention.
Figure 8:
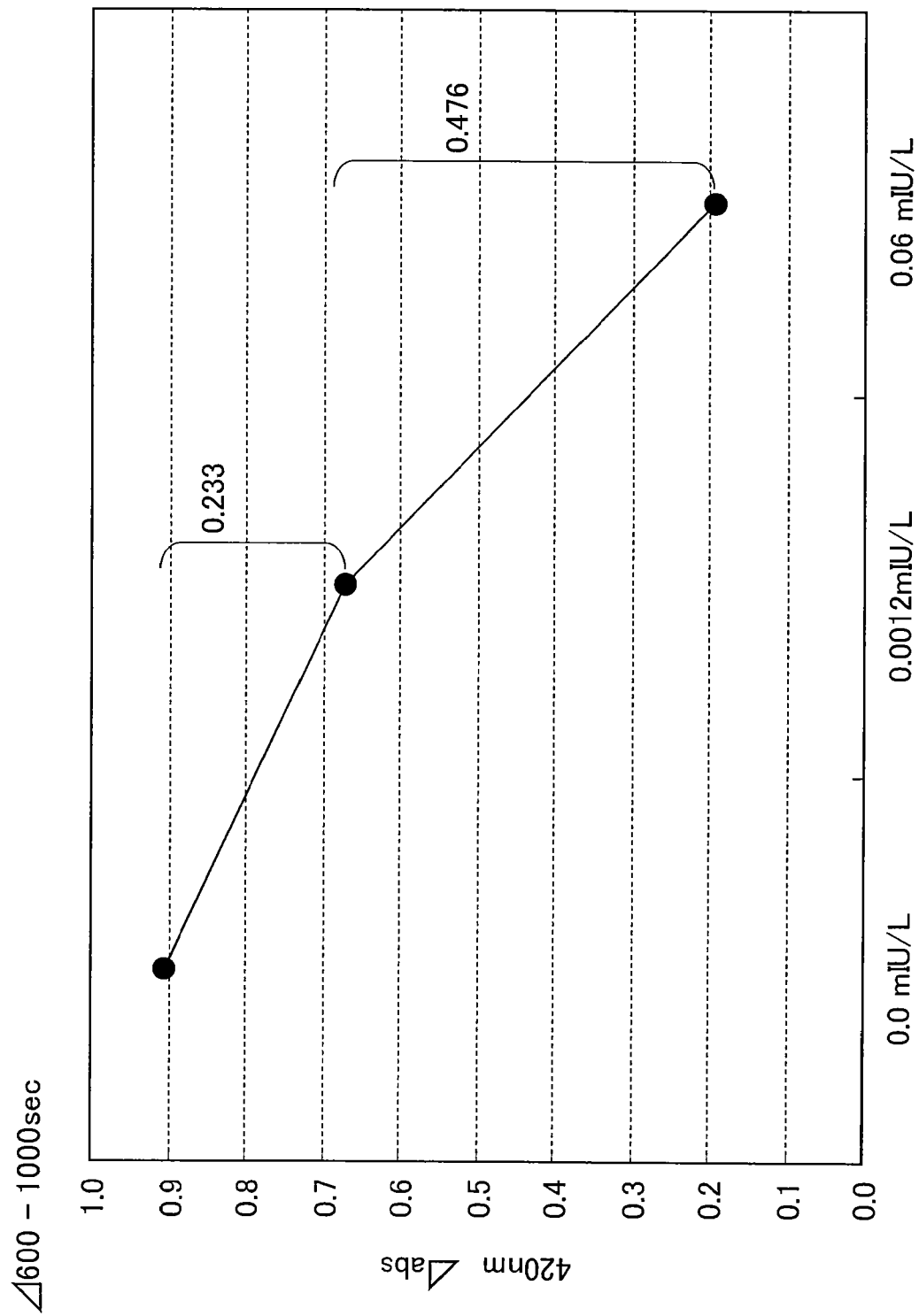
FIG. 8 is a graph showing a correlation between the amount of the target substance and turbidity in a method according to an Example of the present invention.

As shown in FIGS. 6 to 8, the difference of measured values between 0 seconds and 600 seconds, 0 seconds and 1000 seconds, and between 600 seconds and 1000 seconds depended on the amount of the TSH for both samples. Particularly, the difference of the measured values between 600 seconds 1000 seconds was largest, and therefore would allow for the most sensitive detection and quantification. Thus, it is confirmed that one of the plurality of points is preferably the point near the point where the turbidity is a maximum (600 seconds) after applying a magnetic force to the negative control (TSH value is 0).

Evaluation of Reproducibility

By storing the first bound substance, the second bound substance, and the sample in a dark place at 4° C., the determination of turbidity was conducted by the above-mentioned procedure once a day for three days. The results are shown in Table 1.

TABLE 1

|  | ∠0-600 | | ∠0-1000 | | ∠600-1000 | |
| --- | --- | --- | --- | --- | --- | --- |
|  | Average | CV (%) | Average | CV (%) | Average | CV (%) |
| 0.0 mIU/L | 0.5616 | 3.6 | 0.3509 | 3.8 | 0.9124 | 4.3 |
| 0.0012 mIU/L | 0.4376 | 4.5 | 0.2397 | 4.9 | 0.6773 | 5.8 |

As shown in Table 1, the CV (coefficient of variation) was low, below 5.8, for all the points of time in the three days. Therefore, it was confirmed that high reproducibility is provided in the system of the Example.

Example 2

The turbidity of a sample with no TSH was measured in a similar way to the Example 1, except that a neodymium permanent magnet 73 (manufactured by Seiko Sangyo Co., Ltd.) was not attached outside the optical path of the semi-microcell 71 for the spectrophotometer. The result is shown in FIG. 9, with the turbidity of the sample with no TSH in the Example 1.

Figure 9:
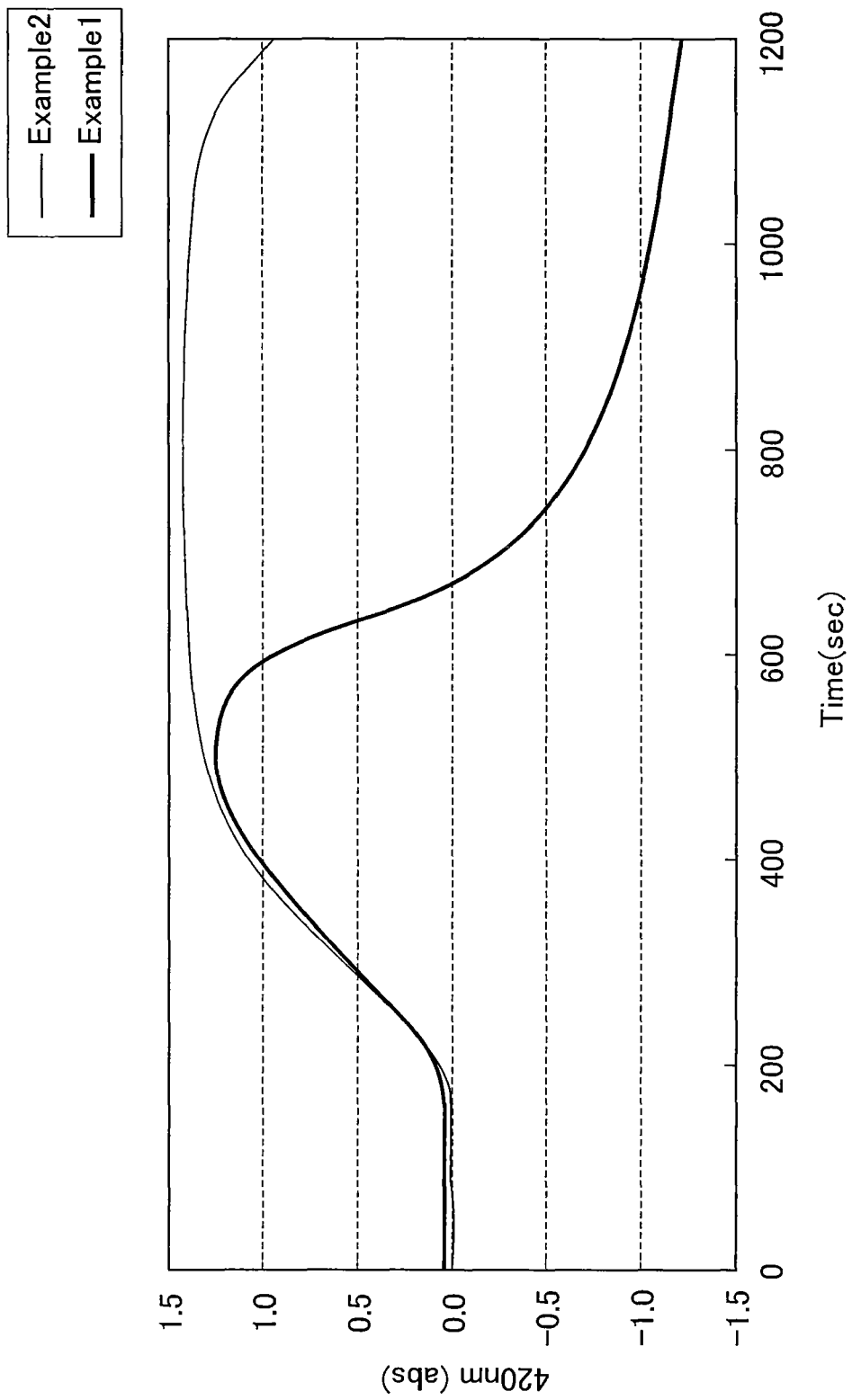
FIG. 9 is a graph showing a correlation between reaction time and turbidity in a method according to another embodiment of the present invention.

As shown in FIG. 9, the turbidity in the Examples 1 and 2 were approximately equal until about 600 seconds, and after 600 seconds, the turbidity in the Example 2 was saturated. The results suggest that, even without applying magnetic force, high sensitive detection or quantification is possible to a certain extent; however, to conduct more sensitive detection or quantification, a magnetic force should be applied and the difference between the measured value at approximately 600 seconds and the measured value at a later point of time should be used.

Comparative Example

Regarding the sample, the amount of TSH was measured using a variety of systems. The detection limits of each system estimated by the results are shown in Table 2.

TABLE 2

| System | Manufacturer Product name Method | OCD Vitros Eci Q CLEIA | GE (ABBOT) Architect EIA | Roche ECLusys ECL-TA |
| --- | --- | --- | --- | --- |
| Detection Limit (mIU/L) | | 0.003 | 0.0025 | 0.005 |
| Incubation time | | 38 min | 29 min | 18 min |
| Process amount (test/h) | | 90 | 200 | 90 |

As shown in Table 2, the detection limit was 0.0025 to 0.005 mIU/L with the conventional systems. Thus, it is confirmed that the detection sensitivity of the Examples, having detected 0.0012 mIU/L, is much higher than the conventional systems.

In addition, differences in turbidity depending on the quantity of TSH were observed at every point, and then it could be used for detection of the TSH in the sample. The time for detection, 1000 seconds, was much shorter than in the conventional systems (see ref. FIG. 10), which requires approximately 38 minutes. Furthermore, the target substance can be detected or quantified conveniently by conducting the above ST10 and ST20 operations on the actual sample.

Therefore, the present invention was proved to be innovative by having a system measuring turbidity without utilizing enzyme-substrate reaction, so that it allows convenient and rapid detection and quantification with much higher sensitivity than the conventional systems.

Example 3

Synthesis of Biotin-Containing Poly(N-isopropyl acrylamide))

In a 200 mL three-neck flask to which a nitrogen gas introduction tube, a thermometer, and a stirrer were provided, 13.6 g of N-isopropyl acrylamide, 0.42 g of biotin monomer [N-biotinyl-N'-methacroyl trimethylene amide] and 0.2 g of 2-aminoethanethiol (manufactured by Wako Pure Chemical Industries, Ltd.) and 0.2 g of azobisisobutyronitrile were dissolved in 100 mL of methyl alcohol and were nitrogen-substituted for 30 minutes. Then, the polymerization reaction was performed at 70° C. for seven hours. The resulting reaction mixture was vacuum concentrated, and the resulting solid was dissolved in acetone, then reprecipitated with diethyl ether. A white precipitate was filtered, and then dried in a vacuum dryer overnight resulting 11.84 g of biotin-containing poly (N-isopropyl acrylamide). The molecular weight of the resulting biotin-containing poly (N-isopropyl acrylamide) was approximately 29,000 (Shodex GPC LF-804, 8 mm ID×300 mm, mobile phase THF).

For the preparation of biotin monomer [N-biotinyl-N'-methacryloyl trimethylene amide], the method disclosed in Japanese Unexamined Patent Application No. 2005-82538, was used.

18 g of N-(3-aminopropyl)methacrylamide hydrochloride, 24 g of biotin, and 30 g of triethylamine were dissolved in 300 mL of N,N-dimethylformamide (DMF), and cooled to 0° C. 28 g of diphenylphosphonyl azide was dissolved in 50 mL of DMF and dripped into the mixture for one hour. After the dripping, the solution was stirred for three hours at 0° C., and further stirred for 12 hours at room temperature (20° C.). Subsequently, the solvent was removed under reduced pressure, and purified by column chromatography using a chloroform-methanol solvent mixture, N-biotinyl-N'-methacryloyl trimethylene amide was obtained.

Preparation of Streptavidin Binding N-Isopropyl Acrylamide 100 mg of biotin-containing poly(N-isopropyl acrylamide) was dissolved in 10 mL of TBS buffer at a concentration of 0.1% (w/v). 15 microliters of streptavidin, dissolved in purified water (purified using Direct-Q (trade name) manufactured by Millipore Corporation) at a concentration of 10 mg/mL, was added to 3 mL of 0.1% biotin-containing poly (N-isopropyl acrylamide), and reacted for 30 minutes without stirring on ice to obtain a TBS solution of streptavidin binding poly(N-isopropyl acrylamide).

Preparation of Mouse Anti-TSH Alpha Antibody Binding Poly(N-Isopropyl acrylamide)

100 microliters of biotinylated mouse anti-TSH alpha antibody (mouse anti-TSH alpha antibody purchased from COSMO BIO Co., Ltd. (item code T103, manufactured by Leinco Technology, Inc) biotinylated by sulfo-NHS-Biotin method (by Asahi Techno Glass Corporation)) was added to 625 microliters of the TBS solution of streptavidin binding poly(N-isopropyl acrylamide) and reacted for 30 minutes in a stationally state on ice to obtain a TBS solution of mouse anti-TSH alpha antibody poly(N-isopropyl acrylamide).

Preparation of Polyacrylic Acid Anti-TSH Beta Antibody Bound Substance

A polyacrylic acid anti-TSH beta antibody bound substance was prepared in a similar way to the Example 2, except that mouse anti-TSH beta antibody was used instead of the mouse anti-TSH alpha antibody.

Detection of TSH Using Anti-TSH Alpha Antibody Binding Poly (N-isopropyl acrylamide)-polyacrylic Acid Anti-TSH Beta Antibody Bound Substance.

Four 1.5 mL tubes with 25 microliters of a TBS solution of mouse anti-TSH alpha antibody binding poly(N-isopropyl acrylamide) (a, b, c and d) were prepared. To each tube, 5 microliters of Vitros TSH calibrator 1 (manufactured by Ortho-Clinical Diagnostic K.K., article code 065002) and 10 microliters of a TBS solution of TSH of different concentrations (a: TSH 0, b: TSH 0.001 microgram/microliter, c: TSH 0.01 microgram/microliter, d: TSH 0.1 microgram/microliter) was added, and 165 microliters of TBS buffer was further added, then still reacted for five minutes on ice. Thereafter, 5 microliters of polyacrylic acid anti-TSH beta antibody bound substance was added to each tube, and left to rest on ice for 30 minutes to obtain test samples.

The cell holder of spectrophotometer UVmini (manufactured by Shimadzu Corporation) was kept warm at 31.5° C. with an incubator. A quartz cell (QS, Hella, optical path length 10 mm) not containing a sample was put in the cell holder, and left at rest for five minutes. Then, 200 microliters of the test sample in the tube a was added to the quartz cell, and the absorbance thereof was measured six minutes later. With the sample in tube b, tube c and tube d, absorbance thereof was measured in a similar way. As a result, the absorbance of the sample in tube a was 0.216, the sample in tube b was 0.199, the sample in tube c was 0.176, and the sample in tube d was 0.168.

The abovementioned results showed that the absorbance changes according to the concentration of TSH; in other words, the concentration of TSH can be determined by measuring the absorbance. Therefore, it was confirmed that the method according to the present invention is a novel method not requiring any special reagent or instrument such as a secondary antibody, luminescent reagent or photodetector, and allowing for quick, inexpensive and convenient detection and quantification of a target substance.

The invention claimed is:

1. A method for detecting a target substance in a sample, comprising steps of:
mixing a first bound substance in which a first substance containing stimuli-responsive polymer binds to a first affinity substance having affinity to the target substance, a second bound substance in which the second bound substance is electrically charged binds to a second affinity substance having affinity to the target substance, and a sample; wherein said the second bound substance inhibits the aggregation of stimuli responsive polymer;
putting the mixture under aggregation conditions of the stimuli-responsive polymer, and determining if the stimuli-responsive polymer is dispersed or not, wherein the first affinity substance and the second affinity substance can simultaneously bind to different sites of the target substance; and determining that the target substance is present in a case in which aggregation inhibition of the stimuli-responsive polymer is confirmed via inhibition of the aggregation of the stimuli responsive polymer by the second bound substance, and that the target substance is not present in a case in which aggregation inhibition of the stimuli-responsive polymer is not confirmed; wherein the step of determining if dispersion is present or not is carried out under aggregation conditions of the stimuli-responsive polymer.

2. The method according to claim 1, wherein the first substance comprises a particulate magnetic material, and the method further comprises a step of separating the aggregated magnetic material by applying a magnetic force.

3. A method for quantifying a target substance in a sample, comprising steps of:
mixing a first bound substance in which a first substance containing stimuli-responsive polymer binds to a first affinity substance having affinity to the target substance, a second bound substance in which the second bound substance is electrically charged binds to a second affinity substance having affinity to the target substance, and a sample; wherein said the second bound substance inhibits the aggregation of stimuli responsive polymer;
putting the mixture under aggregation condition of the stimuli-responsive polymer, and measuring a change of the turbidity of the mixture via inhibition of the aggregation of the stimuli responsive polymer by the second bound substance; and
calculating the amount of a target substance in the sample based on a correlation equation between the amount of the target substance and the turbidity under the aggregation conditions wherein the step of measuring the turbidity is carried out under aggregation conditions of the stimuli-responsive polymer.

4. The method according to claim 3, wherein the first substance comprises a particulate magnetic material, and the method further comprises a step of separating the aggregated magnetic material by applying a magnetic force.

5. A kit for detecting a target substance, comprising: a first bound substance, wherein a first substance including a stimuli-responsive polymer binds to a first affinity substance having affinity to the target substance; and a second bound substance in which a second electrically charged substance binds to a second affinity substance having affinity to the target substance, wherein the first affinity substance and the second affinity substance can bind simultaneously to different sites of the target substance, wherein said kit detects said target substance according to a method for detecting a target substance in a sample, comprising steps of: mixing a first bound substance in which a first substance containing stimuli-responsive polymer binds to a first affinity substance having affinity to the target substance, a second bound substance in which the second bound substance is electrically charged binds to a second affinity substance having affinity to the target substance, and a sample; wherein said the second bound substance inhibits the aggregation of stimuli-responsive polymer; putting the mixture under aggregation conditions of the stimuli-responsive polymer, and determining if the stimuli-responsive polymer is dispersed or not, wherein the first affinity substance and the second affinity substance can simultaneously bind to different sites of the target substance; and determining that the target substance is present in a case in which aggregation inhibition of the stimuli-responsive polymer is confirmed via inhibition of the aggregation of the stimuli-responsive polymer by the second bound substance, and the target substance is not present in a case in which aggregation inhibition of the stimuli-responsive polymer is not confirmed; wherein the step of determining if dispersion is present or not is carried out under aggregation conditions of the stimuli-responsive polymer.

6. The kit according to claim 5, wherein the first substance comprises a particulate magnetic material.

7. The kit according to claim 6, wherein the second substance is a hydrophilic polymer compound.

8. The kit according to claim 7, wherein the second substance is a polyanion or a polycation.

9. The kit according to claim 8, wherein the polyanion is a nucleic acid or a polyacrylic acid.

10. The kit according to claim 8, wherein the polycation is a polyalkylamine or a polyethyleneimine.

11. The kit according to claim 5, wherein the second substance is a hydrophilic polymer compound.

12. The kit according to claim 11, wherein the second substance is a polyanion or a polycation.

13. The kit according to claim 12, wherein the polyanion is a nucleic acid or a polyacrylic acid.

14. The kit according to claim 12, wherein the polycation is a polyalkylamine or a polyethyleneimine.

* * * * *